United States Patent [19]

Miyashita

[11] Patent Number: 5,403,702
[45] Date of Patent: Apr. 4, 1995

[54] CRYSTALS CONSISTING OF AN INDOLINOSPIROBENZOPYRAN DERIVATIVE

[75] Inventor: Akira Miyashita, Ageo, Japan

[73] Assignee: Otsuka Kagaku Kabushiki Kaisha, Osaka, Japan

[21] Appl. No.: 230,885

[22] Filed: Apr. 20, 1994

Related U.S. Application Data

[63] Continuation of Ser. No. 938,041, Nov. 12, 1992, abandoned.

[30] Foreign Application Priority Data

Mar. 13, 1991 [JP] Japan .................................. 3-047203

[51] Int. Cl.$^6$ ............................................. G03C 1/685
[52] U.S. Cl. ........................................ 430/345; 430/495; 430/962; 430/964; 252/586; 346/135.1
[58] Field of Search ............. 430/345, 495, 962, 964; 548/409, 509, 511; 252/586; 346/135.1

[56] References Cited

U.S. PATENT DOCUMENTS

| | | | |
|---|---|---|---|
| 3,100,778 | 8/1963 | Berman | 430/345 |
| 3,642,484 | 2/1972 | Poot et al. | 430/345 |
| 3,785,820 | 1/1974 | Inoue et al. | 430/345 |
| 4,405,733 | 9/1983 | Williams et al. | 430/345 |

FOREIGN PATENT DOCUMENTS

| | | |
|---|---|---|
| 49-30447 | 8/1974 | Japan . |
| 60-54388 | 3/1985 | Japan . |
| 63-5395 | 2/1988 | Japan . |

OTHER PUBLICATIONS

English Language Abstract of JP 61-76490, Kakurai et al., (Apr. 1986).

*Primary Examiner*—Charles L. Bowers, Jr.
*Assistant Examiner*—John A. McPherson
*Attorney, Agent, or Firm*—Armstrong, Westerman, Hattori, McLeland & Naughton

[57] ABSTRACT

The object of the invention is to provide a novel compound suited for use as a thermochromic and photochromic material.

The invention relates to an indolinospirobenzopyran derivative of the general formula

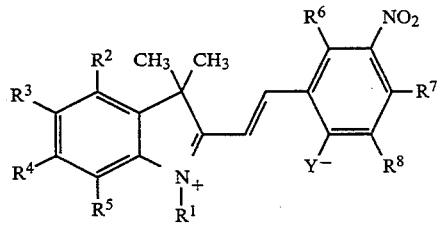

[wherein $R^1$ stands for $C_{1-20}$ alkyl, aralkyl, methacryloxymethyl or methacryloxyethyl; $R^2$, $R^3$, $R^4$, $R^5$, $R^6$ and $R^7$ may for example be hydrogen; $R^8$ may for example be hydrogen or methacryloxymethyl; Y may for example be oxygen or sulfur] and a process for producing the derivative.

3 Claims, 1 Drawing Sheet

CRYSTALS CONSISTING OF AN INDOLINOSPIROBENZOPYRAN DERIVATIVE

This application is a continuation of application Ser. No. 07/938,041, filed Nov. 12, 1992, now abandoned.

TECHNICAL FIELD

The present invention relates to an indolinospirobenzopyran derivative, a process for producing the same, and a thermochromic and photochromic material comprising the derivative.

BACKGROUND ART

The organic compounds undergoing a reversible change of color on exposure to photic or thermal energy which are typical and best known are spiropyran derivatives and G. H. Brown: Photochromism (John Wiley & Sons, Inc., 1971), for one, can be consulted for a specific listing of such derivatives and their physical properties.

However, when an attempt is made to exploit the hitherto-known spiropyran derivatives commercially, for example as photo-responsive materials, they are found to present serious problems. Thus, because the meta-stable species (ring opened isomers) are lacking in thermal stability in solutions as well as in polymeric binders, they tend to promptly revert to the ground state or fade out so that the chromic response at a necessary level cannot be sustained for a sufficient duration.

The object of the present invention is to provide a novel compound suited for use in thermochromic and photochromic materials.

DISCLOSURE OF THE INVENTION

The inventor of the present invention explored in earnest for a spiropyran derivative which would be free from the aforesaid disadvantages and capable of exhibiting a decay-free chromic response and discovered that when an indolinospirobenzopyran derivative of the general formula (2) presented below is dissolved in a polar organic solvent and the resulting solution is irradiated with light of the ultraviolet spectrum, the derivative undergoes ring-opening reaction to give a ring opened isomer [of the general formula (1) presented below]. The inventor further succeeded in the fractional isolation of this isomer in the crystalline form and found that this crystalline isomer is highly stable against heat. The present invention is predicated on the above findings.

The spirobenzopyran derivative of the present invention is a novel compound which has not been described in the published literature and may be represented by the following general formula (1)

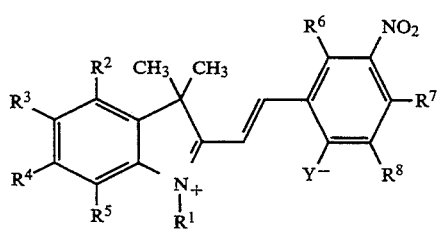

wherein $R^1$ means an alkyl group of 1 to 20 carbon atoms, an aralkyl group, a methacryloxyethyl group or a methacryloxyethyl group. $R^2$, $R^3$, $R^4$ and $R^5$ may be the same or different and each means a hydrogen atom, an alkyl group of 1 to 6 carbon atoms, an aryl group, an aralkyl group, an alkoxy group of 1 to 5 carbon atoms, a halogen atom, a cyano group or a nitro group. $R^6$ and $R^7$ may be the same or different and each means a hydrogen atom, an alkyl group of 1 to 6 carbon atoms, an aryl group, an aralkyl group, a halogen atom, a cyano group or a nitro group. $R^8$ means a hydrogen atom, an alkyl group of 1 to 6 carbon atoms, an alkoxy group of 1 to 5 carbon atoms, a chloromethyl group, a methacryloxyethyl group or a vinyl group. Y means an oxygen atom or a sulfur atom.

As used in this specification, the term aryl group means, inter alia, phenyl and naphthyl, which may be substituted by $C_{1-6}$ alkyl, halogen or $C_{1-5}$ alkoxy. The aralkyl group includes, inter alia, benzyl, phenylethyl, naphthylmethyl, etc., the aromatic ring of which may be substituted by $C_{1-6}$ alkyl, halogen or $C_{1-5}$ alkoxy.

The above spirobenzopyran derivative of general formula (1) can be obtained by dissolving an indolinospirobenzopyran derivative of general formula (2)

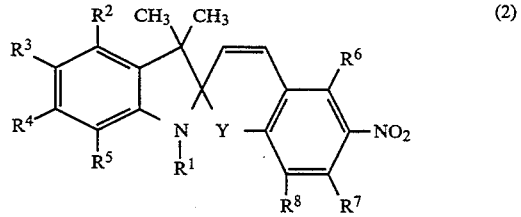

wherein $R^1$, $R^2$, $R^3$, $R^4$, $R^5$, $R^6$, $R^7$, $R^8$ and Y are as defined hereinbefore in a polar organic solvent and irradiating the solution with ultraviolet light.

The inventor knows of one report claiming that when an indolinospirobenzopyran derivative was irradiated with ultraviolet light in methylcyclohexane, there was obtained a pseudo-crystal having properties different from those of the original compound [J. Phys. Chem., 82, 2469 (1978)]. However, the crystal thus reported to be obtained is a pseudo-crystal comprising a two-component system consisting of the starting compound spiropyran and its ring-opening reaction product and is different in chemical composition from the crystal comprised exclusively of said indolinospirobenzopyran derivative which is provided by the present invention.

The above indolinospirobenzopyran derivative of general formula (2) can be produced by condensing a 2,3,3-trimethylindolenium iodide of the general formula

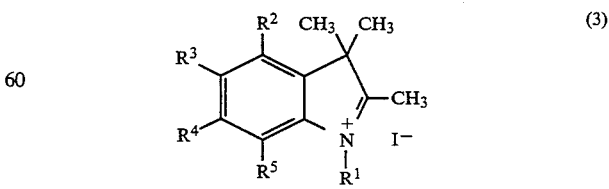

wherein $R^1$, $R^2$, $R^3$, $R^4$ and $R^5$ are as defined hereinbefore with a 5-nitro(thio)salicylaldehyde derivative of the general formula

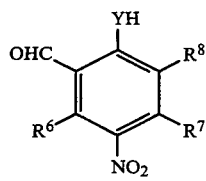

wherein $R^6$, $R^7$, $R^8$ and Y are as defined hereinbefore in the presence of a base such as an amine.

Furthermore, the compound of general formula (2) according to the present invention can also be produced by converting a 2,3,3-trimethylindolenium iodide of general formula (3) to a 2-methylene-3,3-dimethylindolenine derivative of the general formula

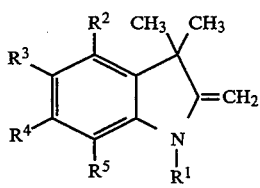

wherein $R^1$, $R^2$, $R^3$, $R^4$ and $R^5$ are as defined hereinbefore, which conversion can be easily achieved by treatment with a base such as an alkali metal hydroxide, and reacting this compound (5) with said 5-nitro(thio)-salicylaldehyde derivative of general formula (4) under heating.

Regarding the above 2,3,3-trimethylindolenium iodide, some species are the known compounds described in Helv. Chim. Acta, 23, 2471 (1940), Japanese Patent Publication No. 58654/1983, Japanese Kokai Patent Publication No. 232461/1987, Japanese Patent Publication No. 21780/1987 and Japanese Kokai Patent Publication No. 267783/1988, for instance, while others are compounds which can be easily prepared in accordance with the processes described in the above literature.

The starting 5-nitrothiosalicylaldehyde derivative of general formula (4) wherein Y means S can be prepared typically by reacting a salicylaldehyde derivative of the general formula

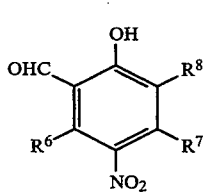

wherein $R^6$, $R^7$ and $R^8$ are as defined hereinbefore with N, N-dimethylthiocarbamoyl chloride, for example in the same manner as described in Japanese Kokai Patent Publication No. 54388/1985, to give a 2-O-(N,N-dimethylthiocarbamoyl)benzaldehyde derivative of the general formula

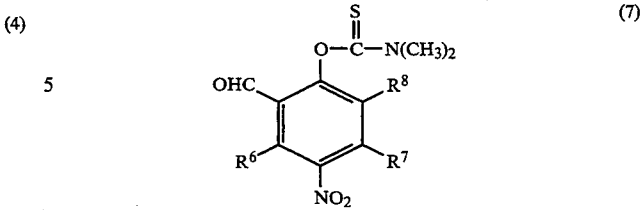

wherein $R^6$, $R^7$ and $R^8$ are as defined hereinbefore, then heating the same to isomerize to a 2-S-(N,N-dimethylthiocarbamoyl)benzaldehyde derivative of the general formula

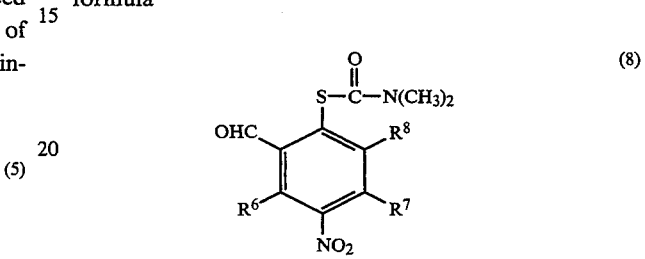

wherein $R^6$, $R^7$ and $R^8$ are as defined hereinbefore, and subjecting the same (8) to alkali hydrolysis.

The crystal comprised of the indolinospirobenzopyran derivative of general formula (1) according to the present invention can be manufactured by dissolving the above compound of general formula (2) in a polar organic solvent and irradiating the resulting solution with ultraviolet light to cause the photoreaction product to crystallize out.

The organic solvent for use in the procedure of dissolving a compound of general formula (2) in an organic solvent and irradiating the same with ultraviolet light is preferably a high-polarity solvent. The high-polarity solvent for this purpose is not limited in kind only if it is able to dissolve the compound (2) and allow the compound of general formula (1) to crystallize out. Among the preferred species of such organic solvent are various lower aliphatic alcohols such as methanol, ethanol, propanol, isopropyl alcohol, n-butanol, isobutyl alcohol, tert-butyl alcohol, amyl alcohol, n-hexanol, cyclohexanol, etc., ethers such as diethyl ether, tetrahydrofuran, dioxane, etc., ketones such as acetone, methyl ethyl ketone, methyl isobutyl ketone, etc., and lower alkyl esters of lower carboxylic acids, such as methyl formate, ethyl formate, methyl acetate, and ethyl acetate.

The concentration of the compound of general formula (2) in the above solvent need only be high enough to allow the photoreaction product to neatly separate out as crystals. Generally speaking, the range of 0.001 mol/l~saturation concentration is preferred.

In the present invention, the compound of general formula (2) is exposed to ultraviolet radiation. The UV light source may be a household fluorescent lamp, a low-pressure mercury vapor lamp, a high-pressure mercury vapor lamp, a super high-pressure mercury vapor lamp or, for that matter, any light source giving an ultraviolet light output, although a super-high-pressure mercury vapor lamp fitted with a band pass filter adapted to transmit an UV emission of the wavelength of about 350 nm is preferably employed.

The present invention has the following advantages.

(1) The production process of the invention achieves both the purification and fixation of the colored form (photomerocyanine) of an indolinospirobenzopyran derivative which is otherwise chromically labile and tends to fade out immediately.

(2) The crystal according to the present invention normally has a deep blue series color and is very stable under light and ordinary temperature conditions but displays a thermochromism such that it fades out instantly on heating to its melting point.

(3) Because the crystal of the invention is exclusively composed of the colored form (photomerocyanine), the color density is high. For example, the molar extinction coefficient at the maximum absorption wavelength of a solution of the crystal in an appropriate solvent at room temperature is several to tens of times as great as the value obtainable by irradiating a solution of the spiropyran compound with ultraviolet light. This is another feature of the invention.

(4) A solution of the crystal of the invention in a suitable solvent normally exhibits a deep blue to deep green color, but on exposure to light of the visible spectrum, fades out to be coloress, demonstrating a photochromism.

An example of application of the crystal of the invention as a thermochromic material is now described.

The crystals according to the invention, either as they are or after pulverization in a mortar or the like, can be uniformly coated on a support or medium to provide a thermochromic material. The medium which can be used for this purpose includes paper, plastic film, a board, a fabric and so on. In coating such a medium with particles of the crystal, a binder such as collodion can be employed where necessary.

BEST MODE FOR CARRYING OUT THE INVENTION

Figure 1:
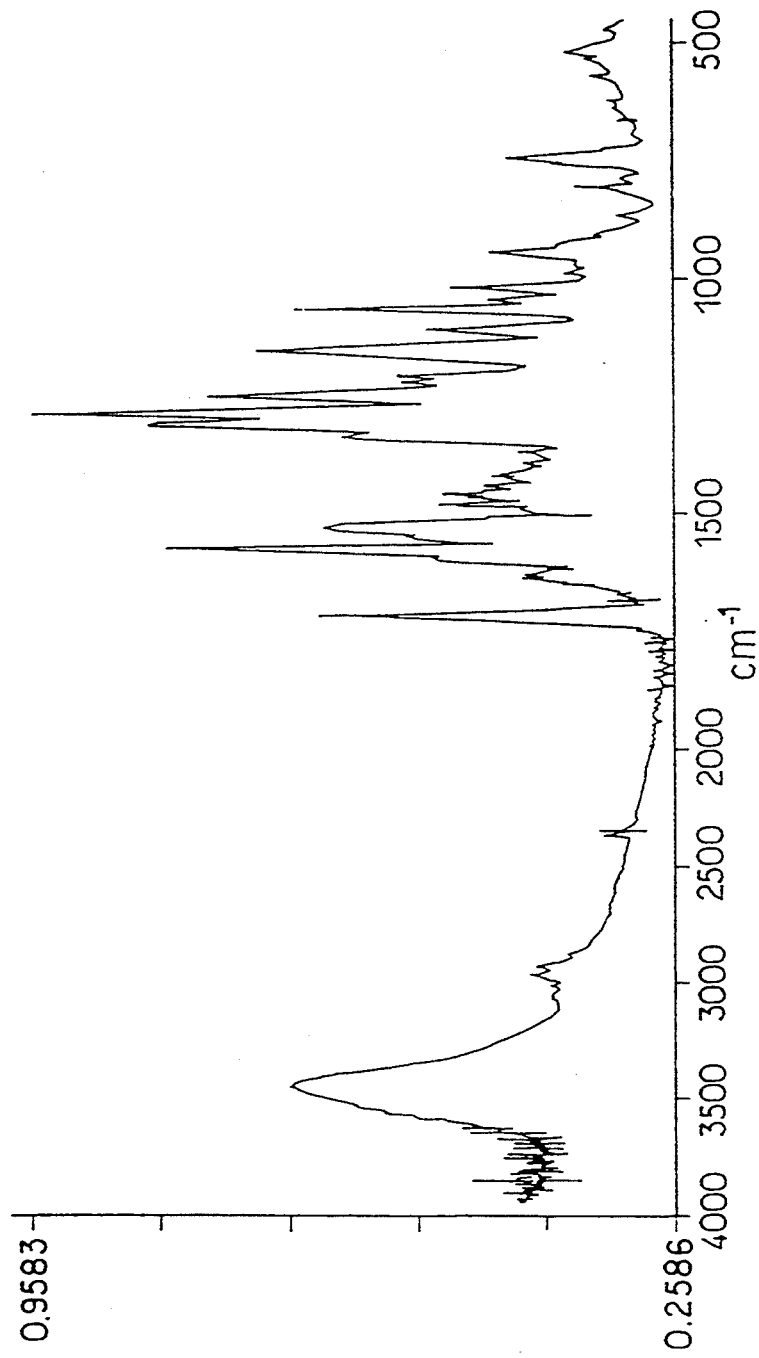
FIG. 1 is an IR spectrum of the crystal composed exclusively of the indolinospirobenzopyran derivate of the invention prepared in Example 8.

The following examples are intended to illustrate the present invention in further detail.

EXAMPLE 1

A mixture of 12.0 g of 5-nitrosalicylaldehyde and 100 ml of chloromethyl methyl ether was cooled on an ice-bath and 43.9 g of anhydrous aluminum chloride was added in small portions. The mixture was stirred at room temperature for 10 minutes and, then, refluxed for 22 hours. This reaction mixture was cooled on an ice-bath and 200 ml of water was added with vigorous stirring, whereupon white crystals separated out. These white crystals were collected, dissolved in hot hexane and filtered and the mother liquor was cooled to give 14.9 g of 3-chloromethyl-5-nitrosalicylaldehyde as colorless needles (Yield 72%).

$^1$H-NMR (CDCl$_3$): δppm 4.72 (s, 2H, —CH$_2$Cl), 8.56 (s, 2H, ArH), 10.00 (s, 1H, CHO), 12.10 (s, 1H, OH)

EXAMPLE 2

In 100 ml of toluene was dissolved 10.5 g of 3-chloromethyl-5-nitrosalicylaldehyde followed by addition of 11.4 g of silver methacrylate. This mixture was heated at 120° C. for 2.5 hours and, then, cooled to room temperature. The resulting precipitate was filtered off and the toluene solution was concentrated under reduced pressure to give 12.7 g of 3-methacryloxymethyl-5-nitrosalicylaldehyde as light yellow powder (Yield 98%).

1H-NMR (CDCl$_3$): δppm 2.00 (t, 3H, CH$_3$), 5.34 (s, 2H, —CH$_2$—), 5.67 (t, 1H, vinyl), 6.22 (m, 1H, vinyl), 8.53 (m, 2H, ArH), 10.00 (s, 1H, CHO)

EXAMPLE 3

In 300 ml of dimethylformamide were dissolved 13.8 g of 3-methacryloxymethyl-5-nitrosalicylaldehyde and 11.2 g of 1,4-diazabicyclo[2.2.2]octane and the solution was heated at 50° C. To this solution was added a solution of 12.9 g of N,N-dimethylthiocarbamoyl chloride in 50 ml of dimethylformamide gradually and the mixture was then heated at 50° C. for 2 hours. The reaction mixture was then diluted with 80 ml of water and extracted with ethyl acetate. The extract was washed with saturated aqueous sodium chloride solution and concentrated under reduced pressure to give 17.6 g of 2-O-(N,N-dimethylthiocarbamoyl)-3-methacryloxymethyl-5-nitrobenzaldehyde (Crude yield 96%).

$^1$H-NMR (CDCl$_3$): δppm 2.0 (m, 3H, CH$_3$), 3.5 (d, 6H, N—CH$_3$), 5.3 (d, 2H, —CH$_2$—), 5.7 (m, 1H, vinyl), 6.2 (m, 1H, vinyl), 8.6 (d, 2H, ArH), 8.7 (d, 1H, ArH), 10.0 (s, 1H, CHO)

EXAMPLE 4

A mixture of 12.6 g of 2-O-(N,N-dimethylthiocarbamoyl)-3-methacryloxymethyl-5-nitrobenzaldehyde and 100 ml of ethanol was refluxed for 21 hours. The reaction mixture was then concentrated under reduced pressure and the residue was dried in vacuo to give 10.7 g of 2-S-(N,N-dimethylthiocarbamoyl)-3-methacryloxymethyl-5-nitrobenzaldehyde (Yield 85%).

$^1$H-NMR (CDCl$_3$): δppm 2.0 (s, 3H, CH$_3$), 3.1 (d, 6H, N—CH$_3$), 5.5 (d, 2H, —CH$_2$—), 5.7 (m, 1H, vinyl), 6.2 (m, 1H, vinyl), 8.6 (d, 1H, ArH), 8.7 (d, 1H, ArH), 10.3 (s, 1H, CHO)

IR (KBr): 1720, 1690, 1660, 1535, 1345 cm$^1$

EXAMPLE 5

To a mixture of 14.1 g of 2-S-(N,N-dimethylthiocarbamoyl)-3-methacryloxymethyl-5-nitrobenzaldehyde and 200 ml of methanol was added 140 ml of 0.64N aqueous sodium hydroxide solution at room temperature. To this reaction mixture was added 380 ml of 0.49N hydrochloric acid to adjust it to pH 2 and the mixture was then concentrated under reduced pressure. The residue was extracted with ether and the extract was washed with water and concentrated under reduced pressure to give 9.79 g of 3-methacryloxymethyl-5-nitrothiobenzaldehyde as orange-colored crystals (Yield 87%).

$^1$H-NMR (CDCl$_3$): δppm 2.0 (m, 3H, CH$_3$), 5.3 (s, 2H, —CH$_2$—), 5.7 (m, 1H, vinyl), 6.2 (m, 1H, vinyl), 8.4 (m, 2H, ArH), 10.1 (s, 1H, CHO)

EXAMPLE 6

To a solution of 16.0 g of 2,3,3-trimethylindolenine in 100 ml of chloroform was added 15.9 g of methyl iodide and the mixture was heated in an autoclave at 80° C. for 21 hours. The resulting precipitate was collected by filtration to give 27.5 g of 1,2,3,3-tetramethylindolenium iodide as white crystals. To the crystals was added 270 ml of 10N aqueous potassium hydroxide solution in a nitrogen atmosphere and the mixture was heated at 50° C. for 2.5 hours. This reaction mixture was then extracted with ether and the extract was dried over magnesium sulfate and concentrated under reduced pressure to give 14.1 g of 2-methylene-1,3,3-trimethylindoline (Yield 81%).

$^1$H-NMR (CDCl$_3$): δppm 1.3 (s, 6H, CH$_3$), 3.0 (s, 3H, N—CH$_3$), 6.5–7.0 (dd, 2H, vinyl), 7.0–7.2 (m, 4H, ArH)

EXAMPLE 7

In 120 ml of 2-butanone were dissolved 14.1 g of 3-methacryloxymethyl-5-nitrothiosalicylaldehyde and 8.7 g of 2-methylene-1,3,3-trimethylindoline and the mixture was refluxed in a nitrogen atmosphere for 20 hours. The reaction mixture was then concentrated under reduced pressure and the residue was purified by silica gel column chromatography to give 15.9 g of 8-methacryloxymethyl-6-nitro-1′,3′,3′-trimethyl-spiro[2H-1-benzothiopyran-2,2′-indoline] as light yellow crystals (Yield 73%).

$^1$H-NMR (CDCl$_3$): δppm 1.24 (s, 3H, CH$_3$), 1.39 (s, 3H, CH$_3$), 1.97 (d, 3H, CH$_3$), 2.67 (s, 3H, N—CH$_3$), 5.15 (dd, 2H, CH$_2$), 5.62 (t, 1H, vinyl), 6.05 (d, 1H, thiopyran), 6.16 (s, 1H, vinyl), 6.51 (d, 1H, thiopyran), 6.65 (t, 1H, indoline), 6.96 (d, 1H, indoline), 7.06 (d, 1H, indoline), 7.17 (t, 1H, indoline), 8.02 (d, 1H, benzothiopyran), 8.08 (d, 1H, benzothiopyran)

EXAMPLE 8

In 30 ml of anhydrous methanol was dissolved 109 mg (0.25 mmol) of 8′-methacryloxymethyl-1,3,3-trimethyl-6′-nitro[(2′H)-1′-benzothiopyran-2,2′-indoline], whereupon a light yellow clear solution was obtained. When this solution was irradiated with ultraviolet light using a 500 W super-high-pressure mercury vapor lamp fitted with a band pass filter adapted to transmit an emission of about 350 nm at room temperature for 3 hours, deep blue crystals separated out. These crystals were recovered by filtration and dried under reduced pressure. In this manner, 23.6 mg of the object product was obtained as deep blue crystals (Yield 22%).

The IR spectrum of this product is shown in FIG. 1.

The deep blue crystals thus obtained were dissolved in deuteroacetone cooled to −40° C. beforehand and the $^1$H-NMR spectrum was determined at this temperature. The results, as well as the mass spectrum, are shown below.

$^1$H-NMR (acetone-d$_6$): δppm 1.86 (s, 6H), 1.88 (s, 3H), 4.26 (s, 3H), 5.36 (s, 2H), 5.60 (s, 1H), 6.26 (s, 1H), 7.66 (m, 2H), 7.88 (m, 4H), 8.60 (s, 1H), 9.75 (d, 1H)

MS (EI, 20 eV), m/z=436 (M+)

The deuteroacetone solution just after NMR spectrophotometry was irradiated with visible light using a 500 W super-high-pressure mercury vapor lamp fitted with a band pass filter adapted to transmit light over 500 nm, whereupon the solution lost its inital deep green color rapidly to become light yellow and clear. The $^1$H-NMR spectrum of this solution was different from that of the previous deep green solution and in complete agreement with that of the starting compound.

The elemental analysis of the deep blue crystal was C:65.96%, H:5.58% and N:6.27%. These results indicated that the crystal obtained in this Example 7 was a crystal composed exclusively of the following excited form (photomerocyanine) of the starting material spiropyran.

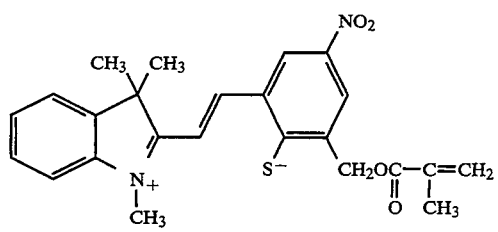

While this deep blue crystal was high in thermal stability, it exhibited thermochromism by fading instantly to a light yellow color at its melting point (130°–135° C.).

EXAMPLE 9

In 3 ml of chloroform were dissolved 1.59 g of 2,3,3-trimethylindolenine and 2.57 g of 2-iodoethanol and the solution was stirred in a sealed tube at 120° C. for 20 hours. The resulting blackish brown oil was dissolved in acetone-methanol followed by addition of ether and the crystals thus obtained were recovered by filtration. In this manner, 2.65 g of N-hydroxyethyl-2,3,3-trimethylindolenium iodide was obtained (Yield 80%).

$^1$H-NMR (CDCl$_3$): δppm 1.53 (s, 6H, CH$_3$), 2.80 (s, 3H, CH$_3$), 3.86 (t, 2H, CH$_2$), 4.57 (t, 2H, CH$_2$), 7.65 (dd, 2H, ArH), 7.83 (dd, 1H, ArH), 7.93 (dd, 1H, ArH)

EXAMPLE 10

In 35 ml of ethanol was dissolved 1.07 g of N-hydroxyethyl- 2,3,3-trimethylindolenium iodide followed by addition of 0.59 g of 5-nitrothiosalicylaldehyde dissolved in 5 ml of 2-butanone and the mixture was stirred at room temperature. To this was added a solution of 0.36 g of triethylamine in 6 ml of ethanol and the mixture was heated and reacted under reflux for 1.5 hours. The reaction mixture was then concentrated and the blackish brown residue was purified by silica gel column chromatography to give 0.63 g of 1-hydroxyethyl-6′-nitro-3,3-dimethylspiro[2′H-1-benzothiopyran-2,2′-indoline] as yellow crystals (Yield 56.8%).

$^1$H-NMR (CDCl$_3$): δppm 1.26 (s, 3H, CH$_3$), 1.41 (s, 3H, CH$_3$), 1.73 (t, 1H, OH), 3.19 (m, 1H, CH$_2$), 3.46 (m, 1H, CH$_2$), 3.80 (m, 2H, CH$_2$), 6.03 (d, 1H, vinyl), 6.59 (d, 1H, ArH), 6.87 (d, 1H, vinyl), 6.89 (t, 1H), 7.09–8.02 (m, 5H)

EXAMPLE 11

In 4 ml of dichloromethane was dissolved 0.40 g of 1-hydroxyethyl-6′-nitro-3,3-dimethylspiro[2′H-1′-benzothiopyran-2,2′-indoline] followed by addition of 0.18 g of triethylamine to give a homogenous solution. To this was added dropwise a solution of 0.18 g of methacryl chloride in 1 ml of dichloromethane and the mixture was stirred at room temperature for 1.5 hours. The reaction mixture was concentrated and the residue was purified by silica gel column chromatography to give 0.40 g of 1-methacryloxyethyl-6′-nitro-3,3-dimethyl-spiro[2′H-1′-benzothiopyran-2,2′-indoline] as yellow crystals (Yield 79.1%).

$^1$H-NMR (CDCl$_3$): δppm 1.21 (s, 3H, CH$_3$), 1.39 (s, 3H, CH$_3$), 1.94 (s, 3H, CH$_3$), 3.32 (m, 1H, CH$_2$), 3.61 (m, 1H, CH$_2$), 4.34 (m, 2H, CH$_2$), 5.59 (m, 1H, vinyl), 6.01 (d, 1H, thiopyran), 6.11 (m, 1H, vinyl), 6.63 (d, 1H), 6.87 (d, 1H), 6.88 (t, 1H), 7.08–8.02 (m, 5H)

EXAMPLE 12

In 10 ml of anhydrous methanol was dissolved thoroughly 112 mg of the 1-methacryloxyethyl-6'-nitro-3,3-dimethylspiro[2'H-1'-benzothiopyran-2,2'-indoline] obtained in Example 11, whereupon a light yellow clear solution was obtained. When this solution was irradiated with ultraviolet light using a 500 W super-high-pressure mercury vapor lamp fitted with a band pass filter adapted to transmit light of the wavelength of about 350 nm at room temperature for 3 hours, deep blue-colored crystals separated out. These crystals were recovered by filtration and dried. In this manner, 18.4 mg of deep blue-colored crystals were obtained (Yield 16%).

The crystals were dissolved in deuterochloroform at −40° C. and the $^1$H-NMR spectrum of the solution was determined at the same temperature. The results are presented below.

$^1$H-NMR (CDCl$_3$):δppm 1.52 (bs, 6H, CH$_3$), 1.90 (s, 3H, CH$_3$), 4.40 (m, 2H, CH$_2$), 4.61 (m, 2H, CH$_2$), 5.56 (s, 1H, vinyl), 6.21 (s, 1H, vinyl), 7.15–7.92 (m, 6H), 7.99 (s, 1H), 8.54 (d, 1H), 9.55 (d, 1H)

The NMR spectrum indicated that the above crystal does not include the starting compound.

When the deuterochloroform solution just after NMR spectrophotometry was irradiated with visible light as in Example 8, the initially deep green solution rapidly underwent fading to become light yellow and clear. The $^1$H-NMR spectrum of this solution was different from that of the previous deep green solution and in complete agreement with that of the starting compound.

The elemental analysis of the above deep blue crystal was C:65.92%, H:5.60% and N:6.35%. These results indicated that the deep blue crystal was a crystal composed of the ring opened isomer (the structural formula below) of the starting compound.

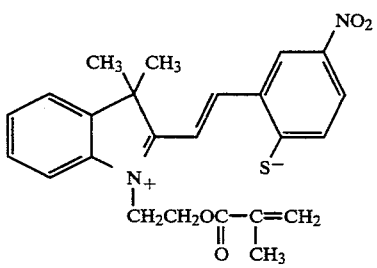

While this crystal was highly stable against heat, it exhibited thermochromism by fading rapidly at its melting point (100°–107° C.).

EXAMPLE 13

To a solution of 1.6 g of 2,3,3-trimethylindolenine in 10 ml of chloroform was added 2.8 g of 1-bromododecane and the mixture was heated in an autoclave at 80° C. for 20 hours. The resulting precipitate was recovered by filtration to give 3.7 g of 1-dodecyl-2,3,3-trimethylindolenium as white crystals. To the crystals thus obtained was added 40 ml of 10N aqueous potassium hydroxide solution in a nitrogen atmosphere and the mixture was heated at 50° C. for 3 hours. The reaction mixture was then extracted with ether and the extract was dried over magnesium sulfate and concentrated under reduced pressure to give 2.7 g of 3,3-dimethyl-1-dodecyl-2-methyleneindoline (Yield 82%).

$^1$H-NMR (CDCl$_3$): δppm 0.87 (t, 3H), 1.25 (s, 18H), 1.30 (s, 6H), 1.62 (m, 2H), 3.03 (m, 2H), 6.60 (dd, 2H), 7.6–8.0 (m, 4H)

EXAMPLE 14

In 6 ml of 2-butanone were dissolved 2.7 g of 3,3-dimethyl-1-dodecyl-2-methyleneindoline and 1.7 g of 5-nitrothiosalicylaldehyde and the mixture was refluxed in a nitrogen atmosphere for 20 hours. The reaction mixture was then concentrated under reduced pressure and the residue was purified by silica gel column chromatography to give 3.0 g of 3,3-dimethyl-1-dodecyl-6'-nitrospiro[2'H-1'-benzothiopyran-2,2'-indoline] as light yellow crystals (Yield 72.7%).

$^1$H-NMR (CDCl$_3$): δppm 0.88 (t, 3H), 1.21 (s, 3H), 1.26 (s, 18H), 1.40 (s, 3H), 1.63 (m, 2H), 3.00–3.25 (m, 2H), 6.02 (d, 1H), 6.45 (d, 1H), 6.79–7.09 (m, 3H), 7.40–7.62 (m, 2H), 7.92–8.13 (m, 2H)

EXAMPLE 15

Using 150 mg of the 3,3-dimethyl-1-dodecyl-6'-nitrospiro[2'H-1'-benzothiopyran-2,2'-indoline] obtained in Example 14, ultraviolet irradiation was performed on an ice-bath for 3 hours as in Example 12, whereupon deep blue crystals separated out. These crystals were recovered by filtration and dried. In this manner, 27.8 mg of the object product was obtained as deep blue crystals (Yield 19.1%).

The above crystalline product was dissolved in deuterochloroform cooled to −40° C. beforehand and the $^1$H-NMR spectrum was determined at the same temperature. The results are presented below.

$^1$H-NMR (CDCl$_3$): δppm 0.90 (t, 3H, CH$_3$), 1.25 (s, 18H, CH$_2$), 1.56 (s, 6H, CH$_3$), 1.70 (bs, 2H, CH$_2$), 4.52 (m, 2H, CH$_2$), 7.30–7.90 (7H), 8.55 (m, 1H), 9.68 (d, 1H)

The above NMR spectrum indicated that the crystal did not include the starting compound.

When the deuterochloroform solution just after NMR spectrophotometry was irradiated with visible light as in Example 8, the initially deep green solution underwent rapid fading to become light yellow and clear. The $^1$H-NMR spectrum of this solution was different from that of the previous deep green solution and in complete agreement with that of the starting compound.

The elemental analysis of the above deep blue crystal was C:73.01%, H:8.30% and N:5.47%. These results indicated that the deep blue crystal was a crystal composed of the following ring opened isomer (the structural formula below) of the starting compound.

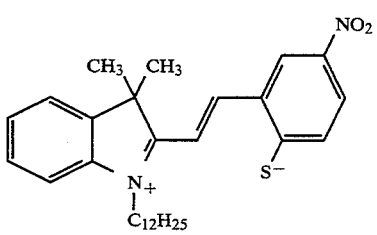

While this crystal was highly stable against heat, it exhibited thermochromism by fading rapidly at its melting point (90°–94° C.).

EXAMPLE 16

To a solution of 4.0 g of 2,3,3-trimethylindolenine in 25 ml of chloroform was added 5.6 g of p-methoxybenzyl bromide and the mixture was heated in an autoclave at 80° C. for 21 hours. The resulting precipitate was recovered by filtration to give 8.5 g of 1-(4-methoxybenzyl)-2,3,3-trimethylindolenium as white crystals. To these crystals was added 85 ml of 10N aqueous potassium hydroxide solution in a nitrogen atmosphere and the mixture was heated at 50° C. for 3 hours. The reaction mixture was then extracted with ether and the extract was dried over magnesium sulfate and concentrated under reduced pressure to give 5.7 g of 3,3-dimethyl-1-(4-methoxybenzyl)-2-methyleneindoline (Yield 80.6%).

$^1$H-NMR (CDCl$_3$): δppm 1.31 (s, 6H), 3.48 (s, 3H), 4.82 (s, 2H), 6.5–6.8 (dd, 2H), 7.0–7.8 (8H)

EXAMPLE 17

In 15 ml of 2-butanone were dissolved 5.7 g of 3,3-dimethyl-1-(4-methoxybenzyl)-2-methyleneindoline and 4.1 g of 5-nitrothiosalicylaldehyde and the mixture was refluxed in a nitrogen atmosphere for 22 hours. The reaction mixture was then concentrated under reduced pressure and the residue was purified by silica gel column chromatography to give 6.2 g of 3,3-dimethyl-1-(4-methoxybenzyl)-6'-nitrospiro[2'H-1'-benzothiopyran-2,2'-indoline] as light yellow crystals (Yield 68.4%)

$^1$H-NMR (CDCl$_3$): δppm 1.25 (s, 3H), 1.40 (s, 3H), 3.80 (s, 3H), 4.44 (s, 2H), 6.05 (d, 1H), 6.50 (d, 1H), 6.7–8.3 (m, 11H)

EXAMPLE 18

Using 172 mg of the 3,3-dimethyl-1-(4-methoxybenzyl)-6'-nitrospiro[2'H-1'-benzothiopyran-2,2'-indoline] obtained in Example 17, ultraviolet irradiation was carried out at room temperature for 2 hours in the same manner as described in Example 12, whereupon deep blue crystals separated out. These crystals were recovered by filtration and dried. In this manner, 45 mg of the object product was obtained as deep blue crystals (Yield 26%).

This crystalline product was dissolved in deuterochloroform cooled to −40° C. beforehand and the $^1$H-NMR spectrum was determined at the same temperature. The results were as follows.

$^1$H-NMR (CDCl$_3$): δppm 1.60 (s, 6H, CH$_3$), 3.71 (s, 3H, CH$_3$O), 5.64 (s, 2H, CH$_2$), 6.9–8.5 (m, 11H), 8.62 (m, 1H), 9.70 (d, 1H)

The above NMR spectrum indicated that the crystal obtained as above did not include the starting compound.

When the deuterochloroform solution just after NMR spectrophotometry was irradiated with visible light as in Example 8, the initially deep green solution underwent rapid fading to become light yellow and clear. The $^1$H-NMR spectrum of this solution was different from that of the previous deep green solution and in complete agreement with that of the starting compound.

The elemental analysis of the above deep blue crystal was C:70.17%, H:5.60% and N:6.40%. These results indicated that the deep blue crystal was a crystal composed of the ring opened isomer (the structural formula below) of the starting compound.

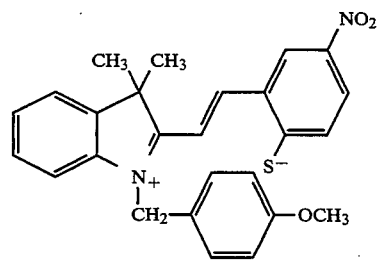

While this crystal was highly stable against heat, it exhibited thermochromism by fading rapidly at its melting point (120°–124° C.).

EXAMPLE 19

Using 303 mg of 1,3,3-trimethyl-6'-nitro[2'H- 1'-benzopyran-2,2'-indoline], ultraviolet irradiation was carried out at room temperature for 2 hours as in Example 12, whereupon deep blue crystals separated out. These crystals were recovered by filtration and dried to give 86 mg of the object product as deep blue crystals (Yield 28%).

This crystalline product was dissolved in deuterochloroform cooled to −40° C. beforehand and the $^1$H-NMR spectrum was determined at the same temperature. The results are presented below.

$^1$H-NMR (CDCl$_3$): δppm 1.59 (s, 6H, CH$_3$), 4.28 (s, 3H, CH$_3$N), 7.28–7.80 (5H), 7.86 (d, 1H), 7.88 (s, 1H), 8.50 (s, 1H), 9.72 (d, 1H).

The above NMR spectrum indicated that the crystal did not include the starting compound.

When the deuterochloroform solution just after NMR spectrophotometry was irradiated with visible light as in Example 8, the initially blue-purple solution underwent rapid fading to become colorless and clear. The $^1$H-NMR spectrum was different from that of the previous blue-purple solution and in complete completion with that of the starting compound.

The elemental analysis of the above blue crystal was C:70.82%, H:5.69%, N:8.81%. These results indicated that the deep blue crystal was a crystal composed of the ring opened isomer (the structural formula below) of the starting compound.

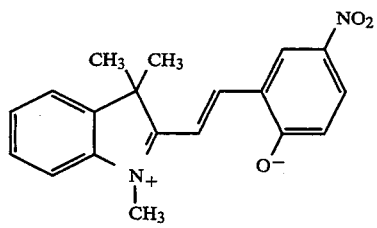

While this crystal was highly stable against heat, it exhibit thermochromism by fading rapidly at its melting point (151°–155° C.).

EXAMPLE 20

The deep blue crystals obtained in Example 8 were milled in a mortar to give a finely divided powder and using a brush, this powder was uniformly spread in a very thin layer on a strip of filter paper. Then, collodion was coated thereon and dried to give a light indigo-colored thermochromic sheet. When this sheet was printed using a commercial thermographic recorder with the

I claim:

1. Colored crystals consisting of an indolinospirobenzopyran derivative of the formula

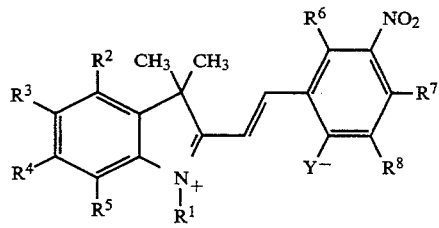

wherein $R^1$ means an alkyl group of 1 to 20 carbon atoms, an aralkyl group, a methacryloxymethyl group or a methacryloxyethyl group; $R^2$, $R^3$, $R^4$ and $R^5$ may be the same or different and each means a hydrogen atom, an alkyl group of 1 to 6 carbon atoms, an alkoxy group of 1 to 5 carbon atoms or a nitro group; $R^6$ and $R^7$ each means a hydrogen atom; $R^8$ means a hydrogen atom, an alkyl group of 1 or 2 carbon atoms, a chloromethyl group, a methacryloxymethyl group or a vinyl group; and Y means an oxygen atom or a sulfur atom.

2. A process for producing the colored crystals of claim 1 characterized by dissolving colorless crystals of the formula

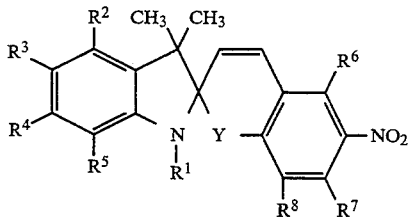

wherein $R^1$ to $R^8$ and Y are as defined in claim 1, in a polar organic solvent and irradiating the resulting solution with ultraviolet light.

3. A thermochromic and photochromic material consisting of the colored crystals of claim 1 coated on a substrate.

* * * * *